US011602276B2

(12) United States Patent
Kumagai et al.

(10) Patent No.: US 11,602,276 B2
(45) Date of Patent: Mar. 14, 2023

(54) MEDICAL IMAGE PROCESSING DEVICE, OCT DEVICE, AND NON-TRANSITORY COMPUTER-READABLE STORAGE MEDIUM STORING COMPUTER-READABLE INSTRUCTIONS

(71) Applicant: NIDEK CO., LTD., Gamagori (JP)

(72) Inventors: Yoshiki Kumagai, Toyokawa (JP); Ryosuke Shiba, Gamagori (JP)

(73) Assignee: NIDEK CO., LTD., Gamagori (JP)

( * ) Notice: Subject to any disclaimer, the term of this patent is extended or adjusted under 35 U.S.C. 154(b) by 285 days.

(21) Appl. No.: 16/833,723

(22) Filed: Mar. 30, 2020

(65) Prior Publication Data

US 2020/0305719 A1 Oct. 1, 2020

(30) Foreign Application Priority Data

Mar. 29, 2019 (JP) .............................. JP2019-066537

(51) Int. Cl.
*A61B 5/00* (2006.01)
*G06T 7/70* (2017.01)
(Continued)

(52) U.S. Cl.
CPC .......... *A61B 5/0066* (2013.01); *A61B 5/0073* (2013.01); *G06T 7/0012* (2013.01);
(Continued)

(58) Field of Classification Search
CPC ... A61B 5/0066; A61B 5/0073; G06T 7/0012; G06T 7/70; G06T 7/246; G06T 11/003;
(Continued)

(56) References Cited

U.S. PATENT DOCUMENTS 8,983,164 B2 * 3/2015 Iwase ................... A61B 3/1225
356/497
9,033,504 B2 * 5/2015 Everett .................. A61B 3/113
351/210
(Continued)

FOREIGN PATENT DOCUMENTS

JP 2013-525035 A 6/2013
JP 2017-064220 A 4/2017
WO WO-2010052929 A1 * 5/2010 ............. A61B 3/102

OTHER PUBLICATIONS

Dec. 27, 2022 Office Action issued in Japanese Patent Application No. 2019-066537.

*Primary Examiner* — Nay A Maung
*Assistant Examiner* — Jose M Torres
(74) *Attorney, Agent, or Firm* — Oliff PLC

(57) ABSTRACT

A target image to be corrected is generated by arranging partial images acquired by scanning a tissue of a living body with light and temporally continuously receiving the light from the tissue. A processor of a medical image processing device performs detecting position shift amounts, acquiring a component, and correcting. In the process of detecting position shift amounts, the processor detects the position shift amounts between the partial images (S3). In the process of acquiring, the processor acquires an assumed result of at least one of a component in the position shift amount caused by movement of the tissue, and a component in the position shift amount caused by a shape of the tissue (S4). In the process of correcting, the processor corrects a position of each of the partial images based on the component in the position shift amount (S7).

13 Claims, 12 Drawing Sheets

(51) Int. Cl.
*G06T 11/00* (2006.01)
*G06T 7/00* (2017.01)

(52) U.S. Cl.
CPC .............. G06T 7/70 (2017.01); G06T 11/003 (2013.01); *G06T 2207/10101* (2013.01); *G06T 2207/30041* (2013.01)

(58) Field of Classification Search
CPC ........... G06T 11/88; G06T 2207/10101; G06T 2207/30041
See application file for complete search history.

(56) References Cited

U.S. PATENT DOCUMENTS

| | | | |
|---|---|---|---|
| 9,408,532 B2 * | 8/2016 | Makihira | A61B 3/10 |
| 9,706,914 B2 * | 7/2017 | Bagherinia | A61B 3/0025 |
| 10,789,721 B2 * | 9/2020 | Iwase | G06T 3/0068 |
| 2010/0110171 A1 * | 5/2010 | Satake | A61B 3/102 |
| | | | 348/78 |
| 2010/0142780 A1 * | 6/2010 | Yasuno | A61B 3/102 |
| | | | 382/131 |
| 2011/0069279 A1 * | 3/2011 | Hacker | A61B 3/102 |
| | | | 351/221 |
| 2011/0267340 A1 * | 11/2011 | Kraus | G06T 7/248 |
| | | | 345/419 |
| 2013/0222566 A1 * | 8/2013 | Murase | G01B 9/02091 |
| | | | 348/78 |

* cited by examiner

63

64

MEDICAL IMAGE PROCESSING DEVICE, OCT DEVICE, AND NON-TRANSITORY COMPUTER-READABLE STORAGE MEDIUM STORING COMPUTER-READABLE INSTRUCTIONS

CROSS REFERENCE TO RELATED APPLICATION

This application is based upon and claims the benefit of priority of Japanese Patent Application No. 2019-066537 filed on Mar. 29, 2019, the contents of which are incorporated herein by reference in its entirety.

BACKGROUND

The present disclosure relates to a medical image processing device, an OCT device, and a non-transitory computer-readable medium storing computer-readable instructions that process image data generated by scanning a tissue of a living body with light.

A medical image photographing device that scans a tissue of a living body with light and continuously receives the light from the tissue so as to generate an image has been known. For example, a photographing device disclosed in Japanese Unexamined Patent Application Publication No. 2017-064220 repeatedly scans a tissue with light and generates data two-dimensional image (partial image) data of the tissue on each scanning line. The photographing device arranges a plurality of the two-dimensional image data and thereby generates three-dimensional image data of the tissue. Further, as a medical image photographing device that scans a tissue with light and generates an image, for example, a scanning laser ophthalmoscope (SLO), a rolling shutter type photographing device and the like have been also known.

SUMMARY

In a case in which the image data is generated by scanning a tissue of a living body with light, the tissue might be moved during the scanning, so that the generated image might be distorted. As a method for correcting the distortion of the image caused by the movement of the tissue, a method that photographs at least a part of an image of a certain tissue, as an image for correction, in a short time shorter than a scanning time necessary for generating a whole of a target image to be corrected, so that the distortion of the target image is corrected based on the image for correction, may be considered. The image for correction is photographed in a short time and therefore the distortion of the image for correction caused by the movement of the tissue is hardly generated. Accordingly, it may be possible to correct the distortion of the target image to be corrected using the image for correction.

However, the method described above needs to photograph the image for correction separately from the target image to be corrected. Thus, for example, improvement of the photographing device, improvement of the photographing method, extension of the photographing time, an increase of man hours for photographing, or the like is needed. Further, in a case in which the image for correction used to correct the target image to be corrected is not photographed, the target image cannot be corrected afterward. Accordingly, the method described above is difficult to appropriately correct the distortion of the target image caused by the movement of the tissue.

Embodiments of the broad principles derived herein provide a medical image processing device, an OCT device, and a non-transitory computer-readable storage medium storing computer-readable instructions that appropriately correct distortion of an image generated by scanning a tissue of a living body with light.

Embodiments of the first aspect provide a medical image processing device that processes data of an image of a tissue of a living body. The image is a two-dimensional image or a three-dimensional image generated by arranging partial images acquired by scanning the tissue of the living body with light and temporally continuously receiving the light from the tissue. The medical image processing device includes a processor that performs: detecting position shift amounts between the partial images forming the image; acquiring a component that acquires an assumed result of at least one of a motion component, which is one component in the position shift amount caused by movement of the tissue during the scanning, and a shape component, which is another component in the position shift amount caused by a shape of the tissue, from the detected position shift amount; and correcting a position of each of the partial images based on the acquired component in the position shift amount.

Embodiments of the second aspect provide an OCT device that photographs an image of the tissue by receiving an interference light of a reference light and a reflection light of a measurement light projected to a tissue of a living body. The OCT device includes a processor that performs: acquiring partial images by scanning the tissue of the living body with the measurement light and temporally continuously receiving the interference light; generating a two-dimensional image or a three-dimensional image by arranging data of the acquired partial images; detecting position shift amounts between the partial images forming the image; acquiring a component that acquires an assumed result of at least one of a motion component, which is one component in the position shift amount caused by movement of the tissue during the scanning, and a shape component, which is another component in the position shift amount caused by a shape of the tissue, from the detected position shift amount; and correcting a position of each of the partial images based on the acquired component in the position shift amount.

Embodiments of the third aspect provides a non-transitory computer-readable storage medium storing computer-readable instructions executed by a processor of a medical image processing device that processes an image of a tissue of a living body. The image is a two-dimensional image or a three-dimensional image generated by arranging data of partial images acquired by scanning the tissue of the living body with light and temporally continuously receiving the light from the tissue. When executed by the processor of the medical image processing device, the instructions causes the medical image processing device to perform processes including: detecting position shift amounts between the partial images forming the image; acquiring a component that acquires an assumed result of at least one of a motion component, which is one component in the position shift amount caused by movement of the tissue during the scanning, and a shape component, which is another component in the position shift amount caused by a shape of the tissue, from the detected position shift amount; and correcting a position of each of the partial images based on the acquired component in the position shift amount.

According to the medical image processing device, the OCT device, and the non-transitory computer-readable medium storing the computer-readable instructions of the present disclosure, the distortion of the image generated by scanning a tissue of a living body with the light can be appropriately corrected.

DETAILED DESCRIPTION

Figure 1:
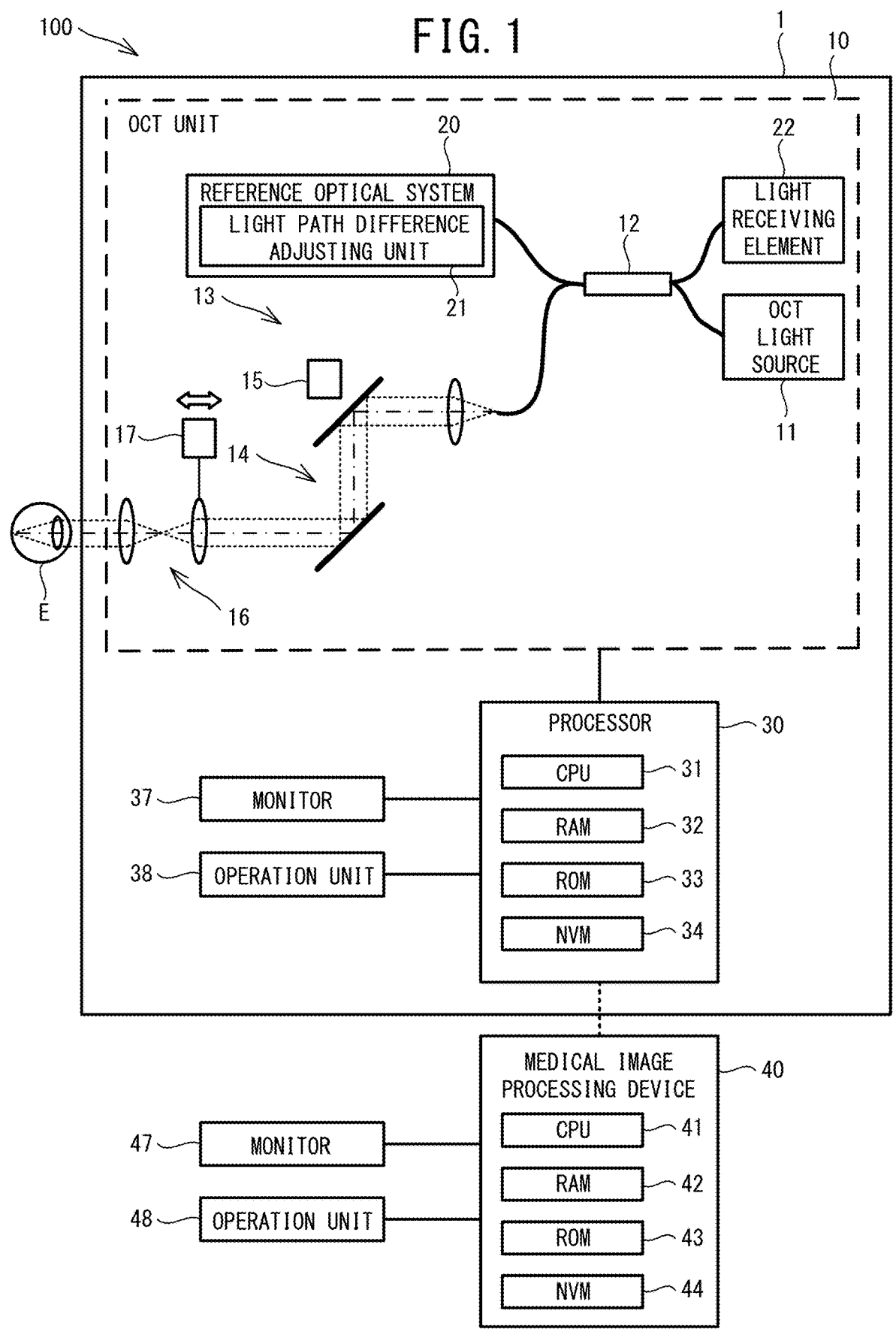
FIG. 1 is a block diagram illustrating a schematic configuration of a medical image acquiring device 100.

A medical image processing device exemplarily described in the present disclosure processes image data of a tissue of a living body. An image to be processed (namely, a target image of which distortion is to be corrected) is a two-dimensional image or a three-dimensional image generated by arranging data of partial images acquired by scanning the tissue of the living body with light and temporally continuously receiving the light from the tissue. A processor of the medical image processing device performs detecting a position shift amount, acquiring a component, and correcting. In the process of detecting position shift amounts, the processor detects the position shift amounts between the partial images forming the image. In the process of acquiring a component, the processor acquires an assumed result of at least one of a component in the position shift amount caused by movement of the tissue during the scanning (hereinafter, referred to as "motion component"), and a component in the position shift amount caused by a shape of the tissue (hereinafter, referred to as "shape component), from the position shift amount detected in the process of detecting position shift amounts. In the process of correcting, the processor correct a position of each of the partial images based on the acquired component in the position shift amount.

The position shift amount detected in the process of detecting position shift amounts includes the motion component, which is one component in the position shift amount caused by the movement of the tissue during the scanning, and the shape component, which is another component in the position shift amount caused by the actual shape of the tissue. Accordingly, the processor acquires the assumed result of at least one of the motion component and the shape component in the position shift amount and corrects the position of each of the partial images based on the assumed component, so that the distortion of the image caused by the movement of the tissue is appropriately corrected.

According to the technique of the present disclosure, an image for which the identical tissue is photographed, to be used for correcting the target image is not needed apart from the target image to be corrected. Accordingly, for example, improvement of the photographing method and extension of the photographing time are not necessary. Further, the target image to be corrected, which was photographed in the past and for which an image to be used for correcting is not photographed, can be also corrected afterward. Thus, the distortion of the image caused by the movement of the tissue during the scanning is appropriately corrected.

Here, as a result of the motion component and the shape component cancelled to each other, a position of which the position shift amount detected in the process of detecting position shift amounts is zero may exist. Thus, in a case in which the position shift amount detected in the process of detecting position shift amounts is zero, each of the motion component and the shape component is not always zero.

In the process of acquiring a component, the processor may acquire the assumed result of the shape component in the position shift amount. In the process of correcting, the processor may correct the position of each of the partial images for forming an aligned image for which the partial images are aligned, based on the shape component.

In each of the partial images for forming the aligned image, both of the position shift caused by the movement of the tissue and the position shift caused by the shape of the tissue are cancelled, respectively. That is, in the aligned image, the distortion caused by the movement of the tissue is cancelled, however information relating to the shape of the tissue disappears. Accordingly, by correcting the position of each of the partial images forming the aligned image based on the shape component, the target image to be corrected can be appropriately corrected into an image for which the distortion is cancelled and the information relating to the shape of the tissue is remained.

A specific method for correcting the position of each of the partial images based on the shape component may be selected as needed. The position shift amounts between the partial images detected in the process of detecting position shift amounts may be defined by a position shift amount of each of the partial images against another partial image compared thereto (for example, another partial image adjacent thereto). The partial image compared thereto denotes, in order to detect the position shift amount of a certain partial image, another partial image of which the position is compared to the certain partial image. Similarly, the assumed shape component in the position shift amount may be defined by the shape component in the position shift amount of each of the partial images against another partial image compared thereto. In this case, in the process of correcting, the processor corrects the position of each of the partial images forming the aligned image into a position shifted from another partial image compared thereto by a distance corresponding to a value of the shape component (in a case in which the value of the shape component is zero, the position of the partial image is set to a position not shifted from another partial image compared thereto). As a result, the distortion of the target image to be corrected caused by the movement of the tissue is appropriately corrected.

Further, the processor may accumulate the shape component in the position shift amount to calculate an accumulated shape component. The shape component in the position shift amount corresponds to an incline of the assumed shape of the tissue. Accordingly, the calculated accumulated shape component indicates the assumed shape of the tissue. In this case, in the process of correcting, the processor corrects the position of each of the partial images forming the aligned image into a position shifted from its aligned position by a distance corresponding to a value of the accumulated shape component (in a case in which the value of the accumulated shape component is zero, the position of the partial image is not changed). As a result, the distortion of the target image to be corrected caused by the movement of the tissue is appropriately corrected.

In the process of acquiring a component, the processor may acquire the assumed result of the motion component in the position shift amount. In the process of correcting, the processor may correct the position of each of the partial images forming the target image to be corrected, into a position where the motion component is cancelled.

As described above, the position shift amount detected in the process of detecting position shift amounts includes the motion component and the shape component. Accordingly, the processor corrects the position of each of the partial images forming the target image to be corrected (original image for which alignment or the like has not been performed), into a position where the assumed motion component is cancelled, so that the distortion of the target image to be corrected caused by the movement of the tissue is appropriately corrected.

A specific method for correcting the position of each of the partial images based on the motion component may be selected as needed. For example, in the process of correcting, the processor corrects the position of each of the partial images forming the target image to be corrected, into a position shifted from another partial image compared thereto by a distance corresponding to a value of the motion component for which its positive or negative is reversed (in a case in which the value of the motion component is zero, the position of the partial image is set to a position not shifted from another partial image compared thereto). As a result, the distortion of the target image to be corrected caused by the movement of the tissue is appropriately corrected.

Further, the processor may accumulate the motion component in the position shift amount to calculate an accumulated motion component. In the process of correcting, the processor may correct the position of each of the partial images forming the target image to be corrected, into a position shifted by a distance corresponding to a value of the accumulated shape component (in a case in which the value of the accumulated motion component is zero, the position of the partial image is not changed). As a result, the distortion of the target image to be corrected caused by the movement of the tissue is appropriately corrected.

The processor may detect the position shift amounts between the partial images based on the movement amount of each of the partial images when aligned. In this case, by using the process of aligning each of the partial images, the position shift amounts between the partial images are appropriately detected. Further, the processor may detect the position shift amount by virtually performing the process of aligning the partial images without actually performing the process of aligning.

A specific method for detecting the position shift amount based on the movement amount of the partial image in the alignment may be selected as needed. For example, the processor may acquire the movement amount of each of the partial images when aligned and detect a value of the acquired movement amount for which its positive or negative is reversed, as the position shift amount.

The processor may detect the position shift amounts between the partial images based on the movement amount of each of the partial images when the position of each of the partial images is aligned to a position where similarity thereof (for example, correlation or the like) to another partial image (for example, another partial image compared thereto described above) is equal to or larger than a threshold. In this case, by using the similarity between the partial images, the position shift amount between the partial images including the motion component and the shape component is appropriately detected.

In the process of detecting position shift amounts, the processor may detect the position shift amounts between the partial images based on the movement amount of each of the partial images when the partial images are aligned such that positions of a specific tissue in the partial images among tissues photographed in the image are close to each other. In this case, since the partial images are (virtually) aligned such that the positions of the specific tissue in the respective partial images are close to each other, the position shift amount between the partial images including the motion component and the shape component is appropriately detected.

The specific tissue used as a reference for the alignment is preferably defined by a tissue commonly exists in each of the partial images. For example, in a case in which the partial image is a tomographic image, the specific tissue may be defined by at least one of a specific layer in the tomographic image and a specific boundary. Further, the number of the specific tissues used as a reference for the alignment is not limited to one. For example, the first to the L-th partial images (L is a natural number) may be aligned based on a first tissue and the (L−m)-th to the N-th partial images (m is a natural number, and N>L) may be aligned based on a second tissue. In this case, even in a case in which there is no tissue, which commonly exists in all of the partial images, the position shift amount between the partial images is appropriately detected.

In the process of acquiring a component, the processor may acquire a function approximated to a transition of the position shift amounts between the partial images, as the assumed result of the shape component in the position shift amount. The position shift amount of the partial image in which the position shift is caused by the movement of the tissue is apt to be out of (separated from) the position shift amount of the partial image in which the position shift is not caused by the movement of the tissue (namely, the partial image in which the position shift is caused by only the actual shape of the tissue). Accordingly, the function approximated to the transition of the position shift amounts is suitably adopted as the assumed result of the shape component for which the motion component is deleted from the position shift amount.

The function approximated to the transition of the position shift amounts may be selected as needed in accordance with the predicted actual shape of the tissue. As described above, the shape component in the position shift amount corresponds to the incline of the assumed shape of the tissue. Accordingly, the accumulated shape component accumulating the shape components in the position shift amounts indicates the assumed shape of the tissue. Thus, for example, in a case in which the actual shape of the tissue is predicted to be approximated to a quadratic function, the function approximated to the transition of the position shift amounts may be set to a linear function. Further, in a case in which the actual shape of the tissue is predicted to be approximated to a cubic function, the function approximated to the transition of the position shift amounts may be set to a quadratic function. That is, a derivative of the function predicted to be approximated to the actual shape of the tissue may be adopted as the function approximated to the transition of the position shift amounts.

In the process of acquiring a component, the processor may acquire the assumed result of the shape component in the position shift amount by deleting, from the position shift amounts between the partial images, a position shift amount of which a difference from another position shift amount is equal to or larger than a threshold. In other words, the processor may acquire the position shift amount of which the difference from another position shift amount is less than the threshold, among the position shift amounts between the partial images, as the assumed result of the shape component. As described above, the position shift amount of the partial image in which the position shift is caused by the movement of the tissue is apt to be out of the position shift amount of the partial image in which the position shift is not caused by the movement of the tissue. Accordingly, by deleting the position shift amount of which the difference from another position shift amount is equal to or larger than the threshold from the position shift amounts between the partial images, the shape component in the position shift amount is appropriately acquired.

In a case in which the shape component is acquired by comparing the difference of the position shift amounts with the threshold, a relationship between the position shift amount to be determined whether it is deleted and the position shift amount compared thereto (namely, "another position shift amount" described above) may be selected as needed. For example, the position shift amount compared thereto may be defined by the position shift amount adjacent to the position shift amount to be determined, in a direction in which the partial images are arranged. That is, the processor may exclude the position shift amount to be determined, in a case in which a difference between the position shift amount to be determined and the position shift amount adjacent thereto is equal to or larger than a threshold. Further, the position shift amount compared thereto may be defined by the position shift amounts around the position shift amount to be determined. That is, the processor may exclude the position shift amount to be determined, in a case in which a difference between an average of the position shift amounts adjacent to the position shift amount to be determined and the position shift amount to be determined is equal to or larger than the threshold.

In the process of acquiring a component, the processor may perform an interpolation process that interpolates the deleted position shift amount in the position shift amounts acquired by deleting the position shift amount of which the difference is equal to or larger than the threshold. In this case, the target image to be corrected is corrected based on the shape component without a blank, and thereby the accuracy of the correction of the image is further improved.

A method for acquiring the assumed result of the shape component in the position shift amount may be modified. For example, the processor may perform a process that excludes an outlier from the position shift amounts acquired in the process of acquiring a position shift amount so as to acquire the assumed result of the shape component. In this case, the processor may perform the process that excludes the outlier by using, for example, a median filter or the like.

In the process of acquiring a component, the processor may acquire a function approximated to a transition of the position shift amounts between the partial images, and acquire a difference of the position shift amount from a value in the acquired function, as the assumed result of the motion component in the position shift amount. In this case, the motion component in the position shift amount is appropriately acquired by using the function. As a specific method for acquiring the function (for example, a method for selecting a function in accordance with the predicted actual shape of the tissue, or the like), a method similar to that described above may be adopted.

A method for acquiring the assumed result of the motion component in the position shift amount may be modified. For example, the processor may acquire the shape component using various methods (for example, a method using a threshold, a method using a median filter, and the like) and then acquire a difference of the position shift amount from the acquired shape component, as the assumed result of the motion component in the position shift amount.

The processor may perform acquiring an accumulated shape component. In the process of acquiring an accumulated shape component, the processor accumulates the shape components acquired in the process of acquiring a component to acquire the accumulated shape component indicating the assumed shape of the tissue. As described above, the accumulated shape component accumulating the shape components is suitably used as information indicating the assumed shape of the tissue. For example, as described above, the accumulated shape component may be used in the process of correcting. Further, the accumulated shape component may be used when a doctor analyses the tissue.

A method for accumulating the shape components may be selected as needed. For example, in a case in which the function approximated to the transition of the position shift amounts is acquired as the assumed result of the shape component, the processor may calculate a primitive function by integrating the acquired function to acquire the accumulated shape component. In this case, the processor can acquire the accumulated shape component appropriately while suppressing an increase of a calculation processing amount. Further, the processor may accumulate the position shift amounts sequentially to acquire the accumulated shape component.

The processor may perform storing a component and correcting afterward. In the storing a component, the processor causes a storage device to store at least one of the shape component and the accumulated shape component. In the process of correcting afterward, the processor corrects the position of each of the partial images based on a component relating to an image of which a subject to be photographed is the same as that of the image to be corrected, among the components stored in the storage device. In this case, in a case in which the same subject to be photographed has been photographed plural times, the processor can perform the process of correcting afterward using the stored component without performing the process of acquiring a component. Accordingly, the image can be corrected appropriately with a simple process. For example, it is suitable to a case in which the image of a certain tissue is regularly photographed to observe the progress thereof.

Further, even in a case in which it is difficult to acquire the component in the position shift amount of the target image to be corrected (for example, a case in which the tissue has been constantly moved during photographing), when the component is stored in the storage device, the target image to be corrected can be appropriately corrected.

The partial image may be a two-dimensional image expanding in a Z direction along an optical axis of the light and an X direction orthogonal to the Z direction. The target image to be corrected may be a three-dimensional image generated by arranging the partial images in a Y direction crossing the Z direction and the X direction. Generally, a scanning time necessary for photographing a three-dimensional image is apt to be longer than that for photographing a two-dimensional image. As the scanning time is longer, the image is apt to be distorted by the movement of the tissue. While, according to the technique of the present disclosure, even in a case in which the three-dimensional image is distorted by the movement of the tissue, an influence of the distortion is appropriately suppressed.

As a photographing device for photographing (generating) the three-dimensional target image to be corrected, various devices may be adopted. For example, an OCT device that photographs a tomographic image of a tissue using a principle of optical coherence tomography may be adopted. Examples of a photographing method by the OCT device include a method for acquiring a three-dimensional tomographic image by two-dimensionally scanning a subject with a spot of a light (measurement light), and a method for acquiring a three-dimensional tomographic image by scanning a subject with light extending in a one-dimensional direction (so-called Line-field OCT). Further, a magnetic resonance imaging (MRI) device or a computed tomography (CT) device may be adopted.

The target image to be corrected may be a two-dimensional image. In this case, as a photographing device for photographing the target image to be corrected, an OCT device that photographs a two-dimensional tomographic image, a scanning laser ophthalmoscope (SLO) that photographs a two-dimensional front image, a rolling shutter type photographing device or the like may be adopted. Further, the photographing device may generate the image data by receiving a reflection reflected by a tissue, or alternatively generate the image data by receiving a light (for example, fluorescence) emitted by a tissue to which a light is irradiated.

Hereinafter, one typical embodiment of the present disclosure will be described. In the present embodiment, an example in which an image of a fundus tissue of a subject eye E photographed by an OCT device is used as a target image to be corrected will be described. However, the target image to be corrected may be an image of a tissue other than a fundus tissue. For example, the target image to be corrected may be an image of a tissue of the subject eye E (for example, anterior ocular segment) other than a fundus tissue, or an image of a tissue of a living body (for example, skin, digestive organ, or brain) other than the subject eye E. As described above, the photographing device that photographs the target image to be corrected is not limited to the OCT device.

A schematic configuration of a medical image acquiring system 100 of the present embodiment is described with reference to FIG. 1. The medial image acquiring system 100 of the present embodiment is provided with a photographing device 1 and a medical image processing device 40. The photographing device 1 acquires (photographs) a plurality of partial images by scanning a tissue of a living body with light and temporally continuously receiving the light from the tissue. In the present embodiment, the partial image is a two-dimensional tomographic image. A target image to be corrected is generated by arranging the partial images. In the present embodiment, the target image to be corrected is a three-dimensional tomographic image. The medical image processing device 40 performs a process of data of the image acquired by the photographing device 1 (for example, a process that corrects distortion of the target image to be corrected, or the like).

A configuration of the photographing device 1 of the present embodiment is described. The photographing device (OCT device) 1 is provided with an OCT unit 10 and a processor 30. The OCT unit 10 is provided with an OCT light source 11, a coupler (beam splitter) 12, a measurement optical system 13, a reference optical system 20, and a light receiving element 22.

The OCT light source 11 emits light (OCT light) for the acquisition of the image data. The coupler 12 branches the OCT light emitted from the OCT light source 11 into a measurement light and a reference light. Further, the coupler 12 of the present embodiment multiplexes the measurement light reflected by a tissue (fundus of the subject eye E in the present embodiment) and the reference light generated by the reference optical system 20 and causes them to interfere. That is, the couple 12 of the present embodiment functions as both of a branching optical element that branches the OCT light into the measurement light and the reference light and a multiplexing optical element that multiplexes a reflection light of the measurement light and the reference light. Here, at least one of the branching optical element and the multiplexing optical element may be modified. For example, an element other than the coupler (for example, circulator, beam splitter, or the like) may be adopted as the optical element.

The measurement optical system 13 introduces the measurement light branched by the coupler 12 into a subject and returns the measurement light reflected by the tissue to the coupler 12. The measurement optical system 13 is provided with a scanning unit (scanner) 14, an irradiating optical system 16, and a focus adjusting unit 17. The scanning unit 14 is driven by a driving unit 15 so as to scan a subject with the measurement light in a two-dimensional direction crossing an optical axis of the measurement light. In the present embodiment, two galvanometer mirrors that polarize the measurement light to different directions respectively are adopted as the scanning unit 14. However, other device (for example, at least one of polygon mirror, resonant scanner, acoustic optical element and the like) that polarizes light may be adopted as the scanning unit 14. The irradiating optical system 16 is arranged at a downstream side (namely, a side of the subject) in a light path with respect to the scanning unit 14 so as to irradiate a tissue with the measurement light. The focus adjusting unit 17 moves an optical member (for example, lens) installed in the irradiating optical system 16 in a direction along the optical axis of the measurement light so as to adjust focus of the measurement light.

The reference optical system 20 generates the reference light and returns the reference light to the coupler 12. The reference optical system 20 of the present embodiment generates the reference light by reflecting the reference light branched by the coupler 12 using a reflection optical system (for example, reference mirror). However, the reference optical system 20 may be also modified. For example, the reference optical system 20 may transmit the light incident from the coupler without reflecting the light and then return the light to the coupler 12. The reference optical system 20 is provided with light path difference adjusting unit 21 that changes a difference between a light path of the measurement light and a light path of the reference light. In the present embodiment, the reference mirror is moved in the optical axis to change the difference of the light paths. A component that changes the difference of the light paths may be provided in the light path of the measurement optical system 13.

The light receiving element 22 receives the interference light of the measurement light and the reference light generated by the coupler 12 to detect an interference signal. The present embodiment adopts a principle of Fourier domain OCT. In the Fourier domain OCT, spectrum intensity (spectrum interference signal) of the interference light is detected by the light receiving element 22, so that a plurality of OCT signals is acquired through the Fourier transform against the spectrum intensity data. As one example of the Fourier domain OCT, Spectral-domain-OCT (SD-OCT), Swept-source-OCT (SS-OCT) or the like can be adopted. Further, for example, Time-domain-OCT (TD-OCT) can be also adopted.

Further, in the present embodiment, a two-dimensional region is scanned with a spot of the measurement light by the scanning unit 14 so that the three-dimensional image is acquired. However, a principle of acquiring the three-dimensional image data may be modified. For example, the three-dimensional image data may be acquired by a principle of Line-field OCT (hereinafter, referred to as "LF-OCT"). In the LF-OCT, the measurement light is irradiated simultaneously on an irradiation line extending in a one-dimensional direction in a tissue, and the interference light of the reflection light of the measurement light and the reference light is received by a one-dimensional light receiving element (for example, line sensor) or a two-dimensional light receiving element. When a two-dimensional measurement region is scanned with the measurement light in a direction crossing the irradiation line, a three-dimensional OCT data is acquired.

The processor 30 controls the photographing device 1. The processor 30 is provided with a CPU 31, a RAM 32, a ROM 33, and a non-volatile memory (NVM) 34. The CPU 31 is a controller. The RAM 32 temporarily stores various information. The ROM 33 stores a program executed by the CPU 31, various initial values, and the like. The NVM 34 is a non-transitory storage medium that can keep the stored contents after the power is shutdown.

A monitor 37 and an operation unit 38 are connected to the processor 30. The monitor 37 is one example of a display unit that displays various images. The operation unit 38 is operated by a user for inputting various instructions of the user into the photographing device 1. For example, various devices such as a mouse, a keyboard, a touch panel, and a foot switch can be adopted as the operation unit 38. The various instructions may be input into the photographing device 1 by a sound input into a microphone.

A schematic configuration of the medical image processing device 40 is described. In the present embodiment, a personal computer (hereinafter, referred to as "PC") is adopted as the medical image processing device 40. However, a device other than the PC may be adopted as the medical image processing device. For example, the photographing device 1 itself may function as the medical image processing device that performs a correction process that corrects distortion of a target image to be corrected. The medical image processing device 40 is provided with a CPU 41, a RAM 42, a ROM 43, and an NVM 44. A medical image processing program for performing a medical image process (see FIG. 5 and FIG. 11) described below may be stored in the NVM 44. Further, a monitor 47 and an operation unit 48 are connected to the medical image processing device 40. The monitor 47 is one example of a display unit that displays various images. The operation unit 48 is operated by a user for inputting various instructions of the user into the medical image processing device 40. Similar to the operation unit 38 of the photographing device 1, various devices such as a mouse, a keyboard, and a touch panel can be adopted as the operation unit 48. Further, the various instructions may be input into the medical image processing device 40 by a sound input into a microphone.

The medical image processing device 40 acquires various data (for example, data of an image photographed by the photographing device 1, or the like) from the photographing device 1. The various data may be acquired through, for example, at least one of wired communication, wireless communication, a detachable storage medium (for example, USB memory) and the like.

Figure 2:
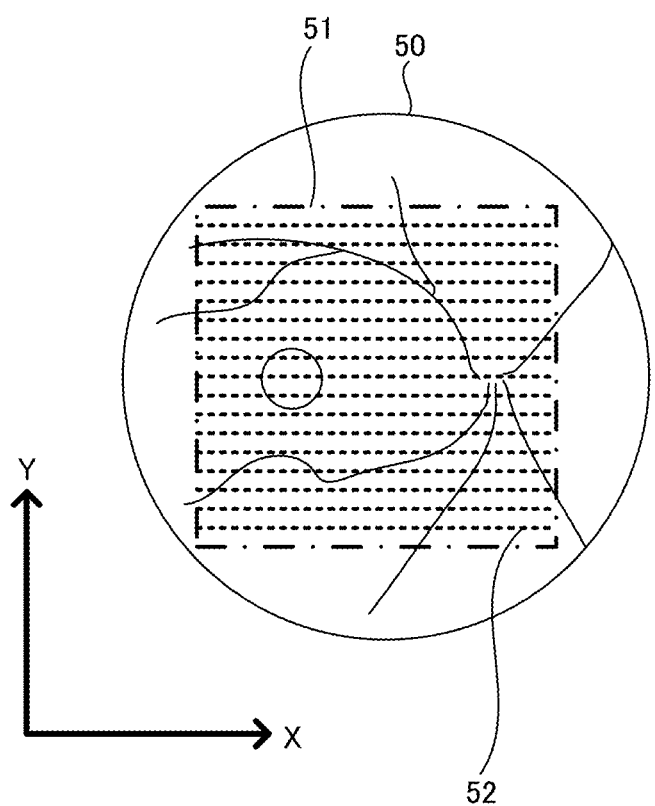
FIG. 2 is a view for describing a method for photographing a three-dimensional image of a tissue 50 of a living body by a photographing device 1.
Figure 3:
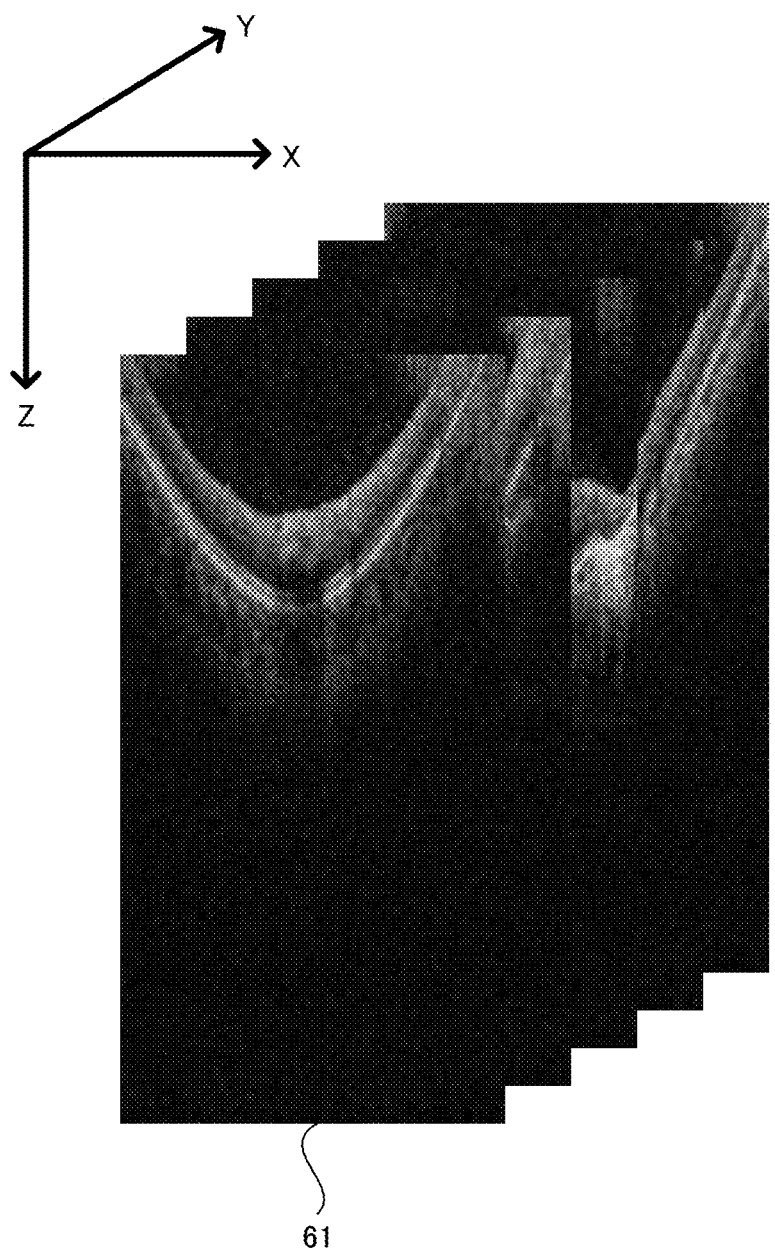
FIG. 3 is a view for describing a state of a plurality of partial images 61 arranged in a Y-direction.

Next, one example of a photographing method of the target image to be corrected for which the distortion is to be corrected by the medical image processing device 40 of the present embodiment, and a configuration of the target image to be corrected will be described with reference to FIG. 2 to FIG. 4. As shown in FIG. 2, the photographing device 1 of the present embodiment scans a two-dimensional region 51 in a tissue 50 of a living body (fundus tissue in the example shown in FIG. 2) with the light (measurement light). Specifically, the photographing device 1 of the present embodiment scans a scanning line 52 extending in a predetermined direction in the region 51 with the light and thereby acquires (photographs) a two-dimensional image that expands in a Z direction along the optical axis of the light and an X direction orthogonal to the Z direction, as a partial image 61 (see FIG. 3). In the example shown in FIG. 2, the Z direction (depth direction) is orthogonal to the two-dimensional region 51, and the X direction is along the scanning line 52. Next, the photographing device 1 moves a position of the scanning line 52 in a Y direction within the region 51 and to acquire the partial image 61 repeatedly. The Y direction crosses (orthogonally in the present embodiment) both of the Z direction and the X direction. As a result, the partial images 61 (two-dimensional tomographic images) passing respective scanning lines 52 and expanding in the depth direction of the tissue is acquired. Next, as shown in FIG. 3, the partial images 61 are arranged in the Y direction, so that the target image to be corrected, which is a three-dimensional tomographic image in the region 51, is generated.

Here, in a case in which the tissue 50 is moved during the scanning, the generated target image to be corrected is distorted. In particular, in the present embodiment, a time for moving the scanning line 52 in the Y direction is longer than a time for scanning one scanning line 52 with the light. Thus, a position shift caused by the movement of the tissue 50 is easily generated between the partial images 61. When the position shift is generated between the partial images 61, a target image 60 to be corrected is distorted.

Figure 4:
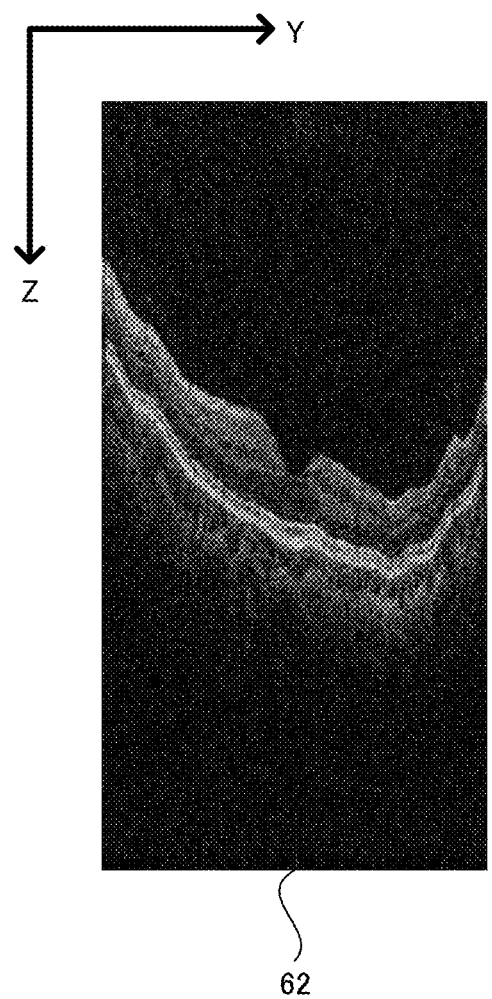
FIG. 4 illustrates one example of a Y-Z tomographic image 62 extracted from a three-dimensional target image to be corrected before distortion thereof is not corrected.

FIG. 4 illustrates one example of a two-dimensional tomographic image 62, which expands in the Y direction and the Z direction (hereinafter, referred to as "Y-Z tomographic image"), extracted from the three-dimensional target image to be corrected before the distortion thereof caused by the movement of the tissue 50 is not corrected. In the example shown in FIG. 4, the tissue 50 is moved while the scanning line 52 is being moved in the Y direction, and as a result, the position shift is remarkably generated between the partial images 61 (see FIG. 3) in particular in the Z direction. As a result, in the Y-Z tomographic image 62 shown in FIG. 4, a layer of the tissue 50 is distorted. In the medical image process described below, the distortion of the target image to be corrected caused by the movement of the tissue 50 is appropriately corrected.

Next, the medical image process of the present embodiment will be described with reference to FIG. 5 to FIG. 10. In the present embodiment, the medical image processing device 40, which is the PC, acquires the data of the target image to be corrected from the photographing device 1 and corrects the acquired target image to be corrected. However, as described above, other device may function as the medical image processing device. For example, the photographing device (OCT device in the present embodiment) 1 itself may perform the medical image process. Also, the processors (for example, the CPU 31 of the photographing device 1 and the CPU 41 of the medical image processing device 40) may work together to perform the medical image process. In the present embodiment, the CPU 41 of the medical image processing device 40 performs the medical image process shown in FIG. 5 based on the medical image processing program stored in the NVM 44.

The CPU 41 acquires the data of the target image to be corrected (S1). For example, a user operates the operation unit 38 or the operation unit 48 (see FIG. 1) to select the image for which the distortion is to be corrected among a plurality of the images. The CPU 41 acquires the data of the image selected by the user as the data of the target image to be corrected. Further, the CPU 41 sets a center coordinate in the target image to be corrected. The center coordinate is set as needed, and is preferably set in a part where the tissue is likely photographed (for example, a center of the image).

And then, the CPU 41 determines whether at least one of a shape component of a position shift amount relating to the target image to be corrected acquired in S1 and information of an accumulated shape component accumulating the shape components is stored in the storage device (for example, NVM 44 or the like) (S2). Although the details are described below, the CPU 41 corrects the distortion of the target image to be corrected based on the shape component in the position shift amount or the accumulated shape component of the partial image 61. In a case in which the shape component or the accumulated shape component of the image of which a subject to be photographed is the same as that of the target image to be corrected has been already stored (S2: YES), the processes that acquire the shape component and the accumulated shape component (S3 to S5) are omitted, and then the process proceeds to S7 (details are described below). As a result, the distortion of the target image to be corrected is appropriately corrected with a simple process. For example, it is suitable to a case in which the image of a certain tissue 50 is regularly photographed to observe the progress thereof. Further, even in a case in which it is difficult to acquire the component in the position shift amount of the target image to be corrected, when at least one of the shape component and the accumulated shape component is stored in the storage device, the target image to be corrected is appropriately corrected. In a case in which both of the shape component and the accumulated shape component relating to the target image to be corrected have not been stored (S2: NO), the CPU 41 performs the processes that acquire the shape component and the accumulated shape component (S3 to S5).

The CPU 41 detects the position shift amounts between the partial images 61 forming the target image to be corrected (S3). Positions of the tissue 50 in the partial images 61 are shifted in accordance with the actual shape of the tissue 50. For example, in a case in which the actual shape of the tissue 50 is inclined to the Y direction, since the partial images 61 are arranged in the Y direction, the positions of the tissue 50 in the partial images 61 are gradually shifted in accordance with the actual shape of the tissue 50. Moreover, in a case in which the tissue 50 is moved during the scanning, the positions of the tissue 50 in the partial images 61 may be shifted. The position shift amounts between the partial images 61 detected in S3 include both of a component in the position shift amount caused by the actual shape of the tissue 50 (hereinafter, referred to as "shape component") and a component in the position shift amount caused by the movement of the tissue 50 during the scanning (hereinafter, referred to as "motion component").

In the present embodiment, the CPU 41 detects the position shift amounts between the partial images 61 based on the movement amount of the respective partial images 61 when the alignment of the partial images is performed such that the positions of the tissue 50 in the partial images 61 are close to each other (S3). Specifically, the CPU 41 of the present embodiment acquires the movement amount of each of the partial images 61 against an image compared thereto (in the present embodiment, another partial image 61 adjacent thereto) when the alignment of the partial images is performed, and then detects a value of the acquired movement amount for which its positive or negative is reversed, as the position shift amount between the partial images 61.

Figure 6:
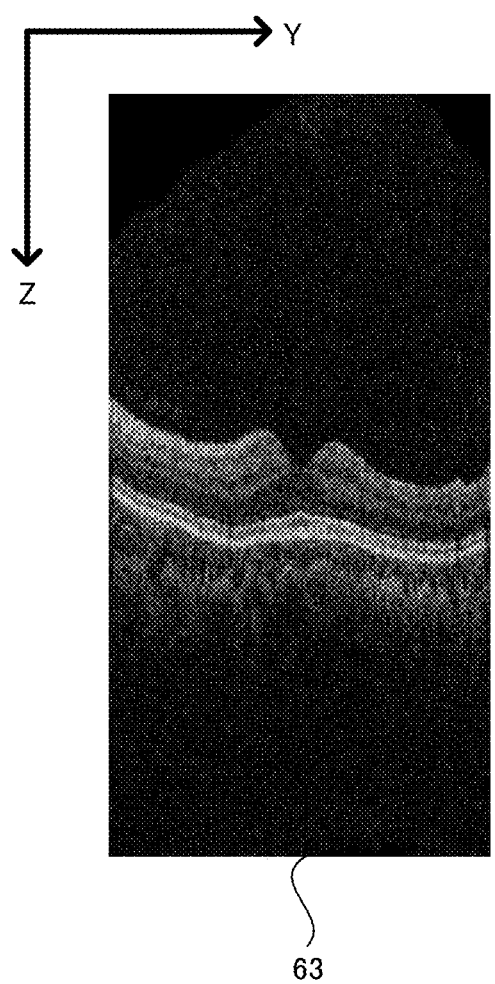
FIG. 6 is a view illustrating a Y-Z tomographic image 63 extracted from the same position as that shown in FIG. 4 after alignment of the partial images 61 is performed.

FIG. 6 is a view illustrating a Y-Z tomographic image 63 extracted from the same position as that shown in FIG. 4 after the alignment of the partial images 61 is performed in the same target image to be corrected as that shown in FIG. 4. As one example, the alignment in the present embodiment is performed based on the partial image 61 at a position of y=y0 (namely, the partial image 61 passing the center coordinate). With the alignment of the tissue 50 in each of the partial images 61, the distortion caused by the movement of the tissue 50 is reduced. As a result, the shape of the tissue 50 photographed in the Y-Z tomographic image 63 shown in FIG. 6 is smooth compared to the shape of the tissue 50 photographed in the Y-Z tomographic image 62 shown in FIG. 4. However, when the alignment of the tissue 50 in each of the partial images 61 is performed, the information relating to the actual shape of the tissue 50 disappears. Thus, in the Y-Z tomographic image 63 shown in FIG. 6, the shape of the tissue 50 becomes closer to a flat shape than the actual shape thereof, compared to the Y-Z tomographic image 62 shown in FIG. 4.

The CPU 41 may use a similarity (for example, correlation or the like) between the partial images 61 when performing the alignment of the partial images 61 in S3. Specifically, the CPU 41 sets each of the partial images 61 at a position in which the similarity thereof to another partial image 61 compared thereto (for example, the partial image 61 adjacent thereto) is equal to or larger than a threshold (in the present embodiment, a position where the similarity is the maximum). As a result, as shown in FIG. 6, both of the position shift of the partial image 61 caused by the movement of the tissue 50 and the position shift of the partial image 61 caused by the actual shape of the tissue 50 are cancelled. Consequently, the position shift amount including the shape component and the motion component is appropriately detected based on the movement amount when performing the alignment.

Also, the CPU 41 may set each of the partial images 61 such that positions of a specific tissue among a plurality of tissues in the respective partial images 61 are close to each other in S3. In this case, the specific tissue used as a reference for the alignment is preferable defined by a tissue commonly exists in each of the partial images 61. For example, as shown in FIG. 3, in a case in which the partial image 61 is a two-dimensional tomographic image, the specific tissue may be defined by at least one of a specific layer in the tomographic image and a specific boundary. Further, the number of the specific tissues used as the reference for the alignment is not limited to one. That is, tissues commonly exist in each of the partial images 61 may be adopted as the reference for the alignment. Further, the CPU 41 may align the first to the L-th partial images 61 (L is a natural number) based on a first tissue and may align the (L-m)-th to the N-th partial images 61 (m is a natural number, and N>L) based on a second tissue. In this case, even in a case in which there is no tissue, which commonly exists in all of the partial images 61, the alignment of the partial images 61 is appropriately performed.

In S3 of the present embodiment, the CPU 41 performs the alignment of the partial images 61 such that the position of each of the partial images 61 is matched with the partial image 61 adjacent thereto. However, another partial image 61 compared thereto when the alignment of each of the partial images 61 is performed is not limited to the partial image 61 adjacent thereto. For example, the CPU 41 may perform the alignment of each of the partial images 61 by using the partial image 61 of which the scanning time is close to each of the partial images 61, as an image compared thereto.

Further, FIG. 6 illustrates one example of the Y-Z tomographic image 63 of an image (hereinafter, referred to as "aligned image") for which the alignment of the partial images 61 has been actually performed. However, the CPU 41 may detect the position shift amount by virtually performing the alignment of the partial images 61 without actually performing the alignment.

In S3 of the present embodiment, the alignment of the partial images 61 is performed by moving each of the partial images 61 parallel to the Z direction. However, the direction in which each of the partial images 61 is moved in the alignment process in S3 is not limited to the Z direction. For example, the CPU 41 may move each of the partial images 61 in the Z direction and the X direction. The CPU 41 may rotate each of the partial images 61. The CPU 41 may perform a deforming process including at least one of correcting distortion, enlarging, and shrinking to the partial images 61. The CPU 41 may use the affine transformation or the like in the process of moving or deforming described above.

Figure 7:
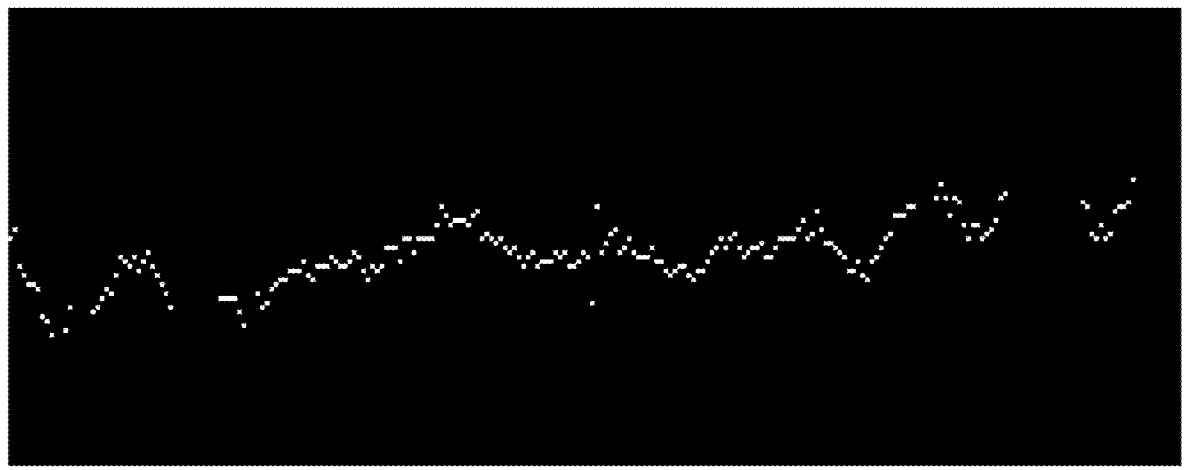
FIG. 7 is a graph illustrating one example in which respective movement amounts of the partial images 61 are plotted, when the alignment of the partial images 61 is performed.

FIG. 7 is a graph illustrating one example in which respective movement amounts of the partial images 61 from an image compared thereto are plotted, when the alignment the partial images 61 is performed such that the positions of the tissues 50 in the partial images 61 are close to each other. In FIG. 7, a horizontal axis denotes the Y direction and a vertical axis denotes the movement amount of each of the partial images 61 from the image compared thereto. The movement amount of each of the partial images 61 from the image compared thereto when the alignment of each of the partial images 61 is performed (specifically, a value of the movement amount for which its positive or negative is reversed) corresponds to the position shift amounts between the partial images 61 in the target image to be corrected (namely, the position shift amount of each of the partial images 61 from the image compared thereto). As described above, when the alignment of the partial images 61 is performed, the shape of the tissue 50 becomes closer to a flat shape than the actual shape thereof. Accordingly, a value (namely, shape component) in which the component (motion component) of the position shift amount caused by the movement of the tissue 50 is deleted from the position shift amount (movement amount) of the partial image 61 exemplarily shown in FIG. 7 corresponds to an incline of the shape of the tissue 50. The position shift amount of the partial image 61 including the motion component is apt to be out of (separated from) the position shift amount of the partial image 61 not including the motion component (namely, the position shift amount caused by only the actual shape of the tissue 50).

Figure 5:
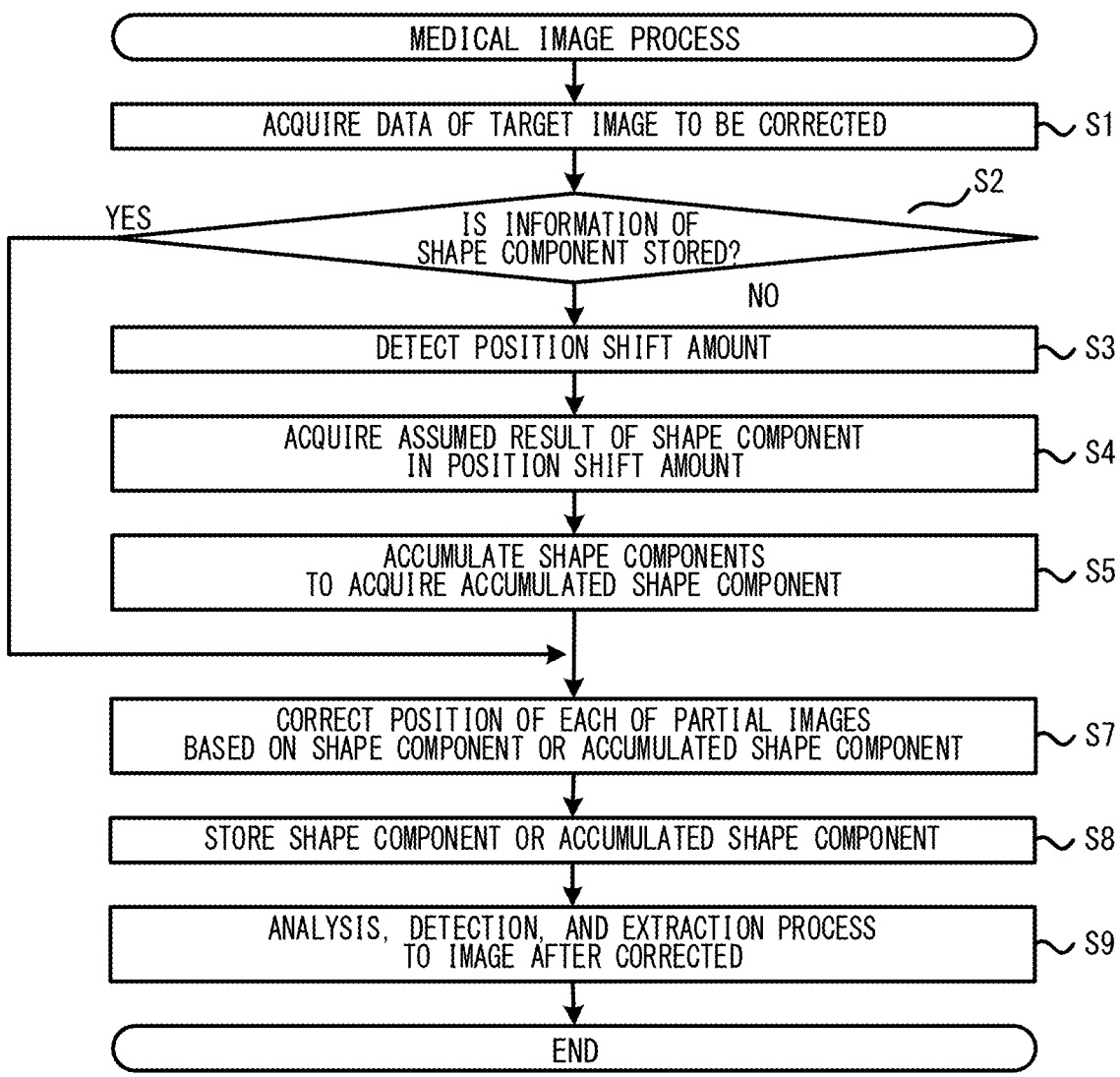
FIG. 5 is a flowchart illustrating a medical image process performed by a medical image processing device 40.
Figure 8:
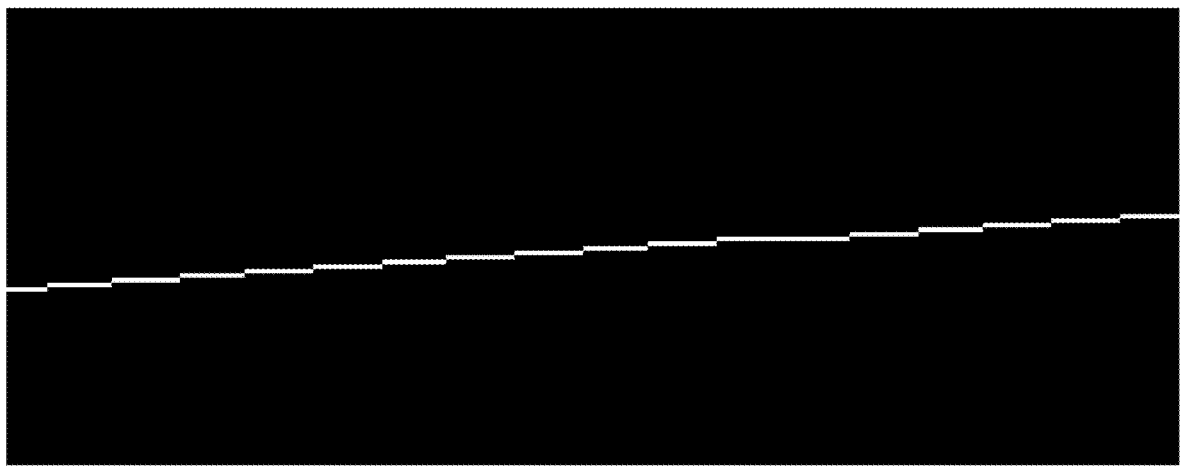
FIG. 8 is a graph illustrating a function f(y) approximated to the movement amount (position shift amount) shown in FIG. 7.
Figure 9:
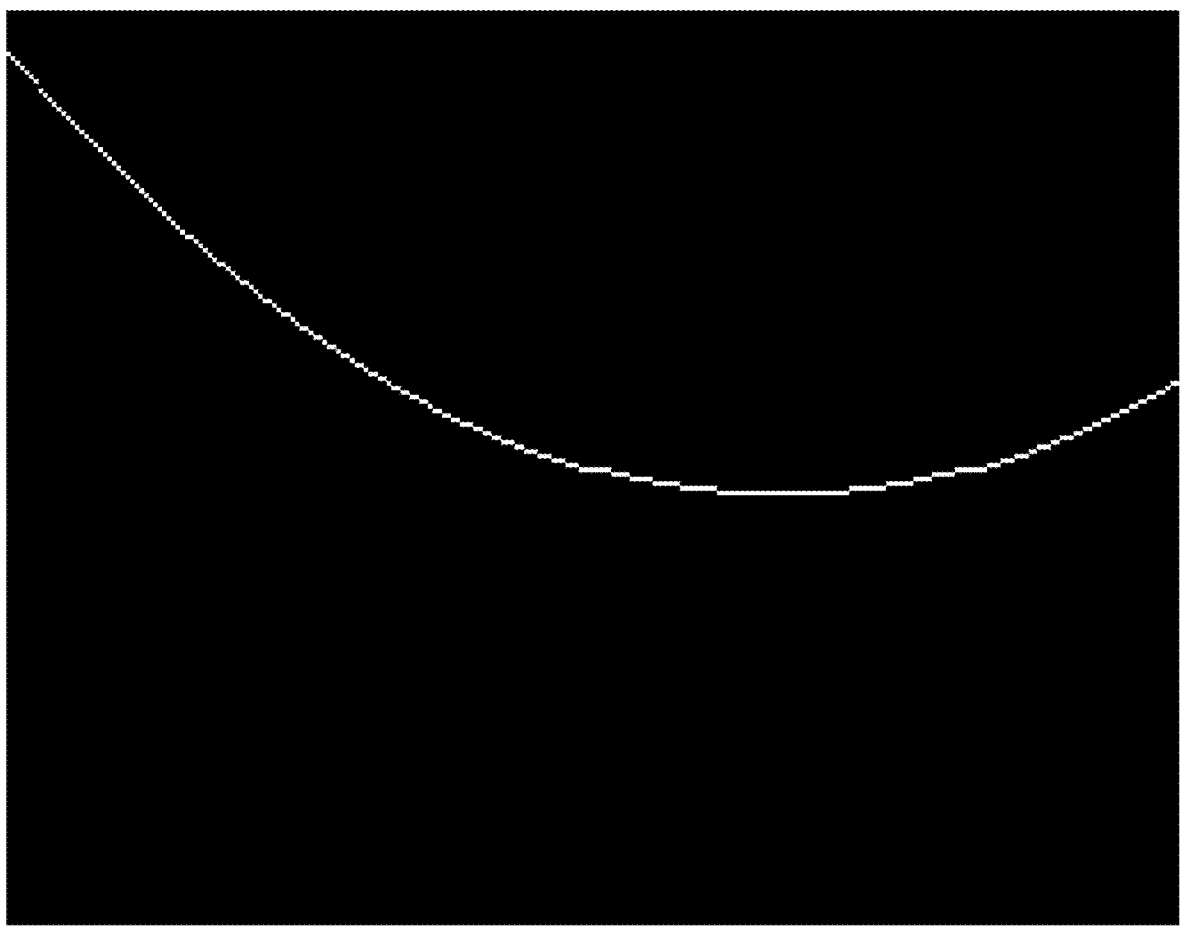
FIG. 9 is a graph illustrating a primitive function F(y) of the function f(y) shown in FIG. 8.

The description is returned to FIG. 5. The CPU 41 acquires an assumed result of the shape component from the position shift amount (see FIG. 7) detected in S3 (S4). Specifically, the CPU 41 of the present embodiment acquires a function approximated to a transition (see FIG. 7) of the position shift amounts between the partial images 61, as the assumed result of the shape component in the position shift amount. FIG. 8 is a graph illustrating a function f(y) approximated to the position shift amount (movement amount) shown in FIG. 7. As described above, the position shift amount including the motion component is apt to be out of the position shift amount not including the motion component. Accordingly, with the function approximated to the transition of the position shift amounts, the outlier is excluded, and thereby the assumed result of the shape component in the position shift amount is appropriately acquired.

And then, the CPU 41 accumulates the shape components in the position shift amounts acquired in S4 to acquire an accumulated shape component (S5). Specifically, the CPU 41 of the present embodiment calculates a primitive function F(y) (see FIG. 9) by integrating the function f(y) (see FIG. 8) approximated to the transition of the position shift amounts so as to acquire the accumulated shape component. As described above, the function f(y) (see FIG. 8) that indicates the assumed result of the shape component in the position shift amount corresponds to the incline of an assumed shape of the tissue. Accordingly, the primitive function F(y) (namely, accumulated shape component) acquired by integrating and accumulating the function f(y) indicates the assumed shape of the tissue.

In the present embodiment, a derivative f(y) (see FIG. 8) approximated to the transition of the position shift amounts and the primitive function F(y) (see FIG. 9) acquired as the accumulated shape component are selected in accordance with the predicted actual shape of the tissue 50. Specifically, in the present embodiment, a sectional shape of the tissue 50 of the fundus photographed in the target image to be corrected is predicted to be approximated to a quadratic function. Thus, in the present embodiment, in order to set the primitive function F(y) to a quadratic function, the derivative f(y) approximated to the transition of the position shift amounts is set to a linear function. However, the derivative f(y) is not limited to a linear function, and the primitive function F(y) is not limited to a quadratic function. For example, in a case in which the shape of the tissue 50 is predicted to be approximated to a cubic function, the derivative f(y) may be set to a quadratic function. That is, the derivative of the function that is predicted to be approximated to the actual shape of the tissue 50 may be adopted as a function that is approximated to the transition of the position shift amounts.

In the present embodiment, the sectional shape of the tissue 50 of the fundus photographed in the target image to be corrected can be predicted to be approximated to a quadratic function in advance, and thereby the derivative f(y) is set to a linear function. However, the derivative f(y) may be modified in accordance with the shape of the tissue 50 as needed. For example, the partial images 61 arranged in the Y direction may be scanned with the light to acquire the two-dimensional Y-Z tomographic image, and then the derivative f(y) and the primitive function F(y) may be set as needed based on the shape of the tissue 50 photographed in the acquired Y-Z tomographic image. In this case, the function is approximately set in accordance with the shape of the tissue 50. Further, the derivative f(y) and the primitive function F(y) may be set based on the shape of the tissue 50 photographed in at least one of the partial images (X-Z tomographic image in the present embodiment) included in the target image to be corrected.

The description is returned to FIG. 5. The CPU 41 corrects the position of each of the partial images 61 based on the shape component in the position shift amount (S7). Specifically, in the present embodiment, the CPU 41 corrects the position of each of the partial images 61 forming the aligned image (in the present embodiment, a three-dimensional image from which the Y-Z tomographic image 63 shown in FIG. 3 is extracted) for which the position of each of the partial images 61 has been aligned, into a position shifted from each of the aligned position by a distance corresponding to a value of the accumulated shape component (see FIG. 9).

Figure 10:
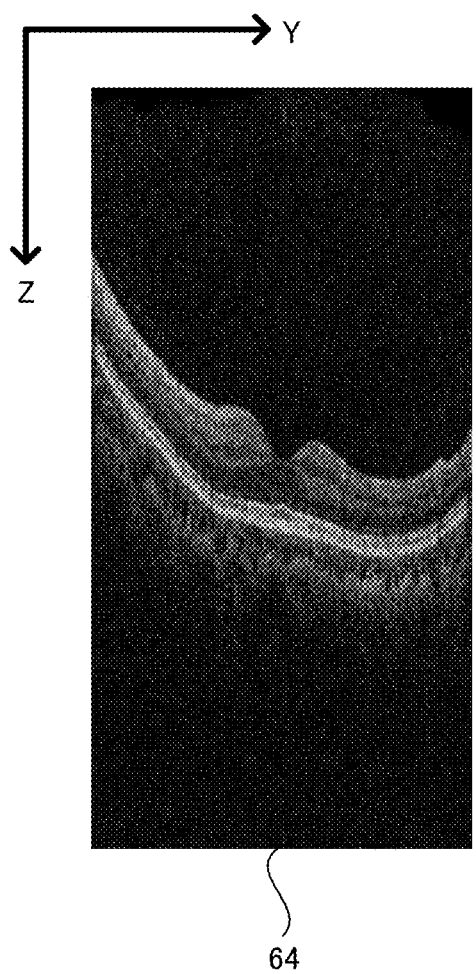
FIG. 10 is a view illustrating a Y-Z tomographic image 64 extracted from the same position as that shown in FIG. 4 and FIG. 6 after a position of each of the partial image 61 is corrected based on a shape component.

FIG. 10 is a view illustrating a Y-Z tomographic image 64 extracted from the same position as that shown in FIG. 4 and FIG. 6 after the position of each of the partial image 61 of the same target image to be corrected as that shown in FIG. 4 and FIG. 6 is corrected based on a shape component. As shown in FIG. 10, the position of each of the partial images is corrected based on the shape component, so that the distortion of the image caused by the movement of the tissue 50 is appropriately corrected while keeping the shape of the tissue 50 close to the actual shape thereof. Further, the CPU 41 may perform a process that smooths the shift between the partial images 61 adjacent to each other in the target image to be corrected for which the position of each of the partial images 61 is corrected in S7. In this case, the corrected image becomes smoother.

In S7, the position of each of the partial images 61 may be corrected using the shape component instead of the accumulated shape component. In this case, the CPU 41 corrects the position of each of the partial images 61 forming the aligned image, into a position shifted from the image compared thereto by a distance corresponding to a value of the shape component. As a result, similar to the example shown in FIG. 10, the distortion of the target image to be corrected caused by the movement of the tissue 50 is appropriately corrected. Further, in a case in which the position of each of the partial images 61 is corrected using the shape component, the process of S5 may be omitted. Further, in a case in which the correction is performed using the shape component or the accumulated shape component stored in the storage device (S2: YES, S7), the aligned image may be generated in S7 instead of S3.

And then, the CPU 41 causes the storage device (for example, NVM 44 or the like) to store at least one of the shape component acquired in S4 and the accumulated shape component acquired in S5 with being linked to a subject to be photographed (S8). The stored parameter is used thereafter when performing the correction of an image of which the subject to be photographed is the same.

And then, the CPU 41 performs at least one of an analysis process, a detection process, and a process that extracts any tomographic image, to the image for which the distortion thereof has been corrected in S7 (S9). The distortion of the image to be processed has been appropriately corrected, and therefore the accuracy of the various processes such as the analysis process can be secured. Examples of the analysis process include various processes such as a process that analyzes a distribution of a thickness of a specific layer. Examples of the detection process include various processes such as a process that detects a specific layer or a specific boundary in the tissue 50. In a case in which any image is extracted, the extracted image may be either a two-dimensional image or a three-dimensional image.

Figure 11:
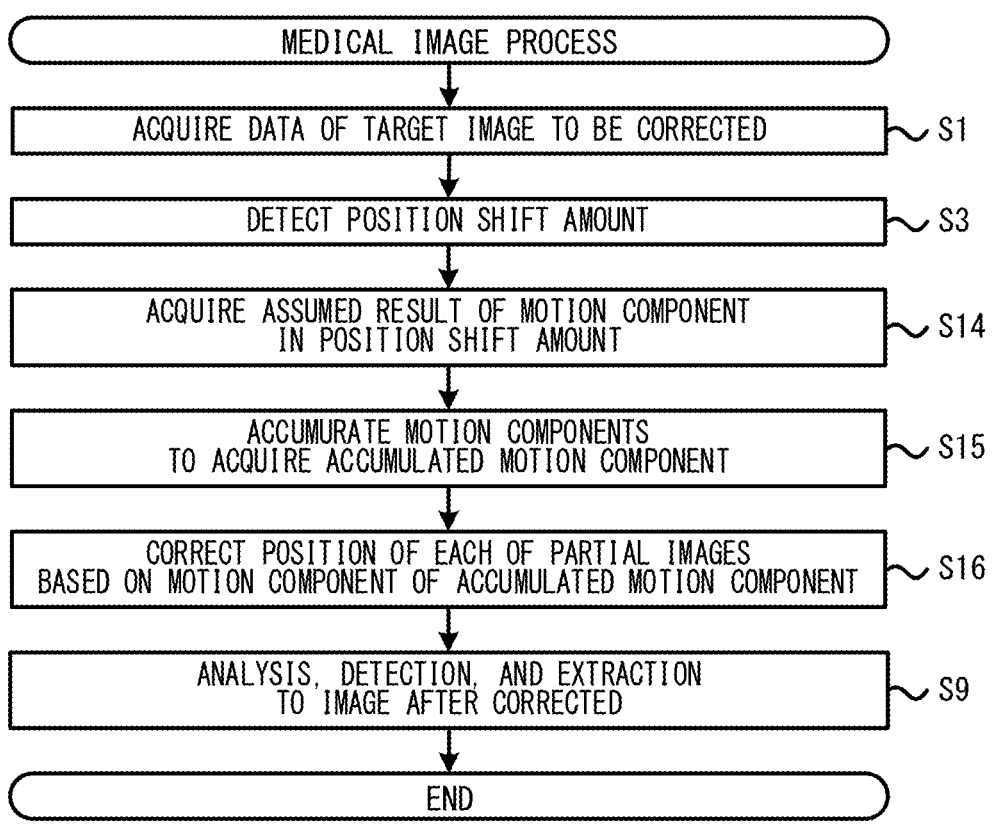
FIG. 11 is a flowchart illustrating one example of a modified example of the medical image process exemplarily shown in FIG. 5.

The technique disclosed in the embodiment described above is merely one example. Accordingly, the technique exemplarily described in the embodiment described above may be modified. FIG. 11 is a flowchart illustrating one example of a modified example of the medical image process exemplarily shown in FIG. 5. A part of the process shown in FIG. 11 may adopt a similar process to that in the medical image process exemplarily shown in FIG. 5. Accordingly, a process number which is the same as that in FIG. 5 is assigned to the process shown in FIG. 11, which is performed similar to the process exemplarily shown in FIG. 5, and the description thereof is therefore omitted or simplified.

In the modified example of the medical image process shown in FIG. 11, the CPU 41 corrects the position of each of the partial images 61 forming the target image to be corrected, based on the motion component in the position shift amount. The CPU 41 acquires the data of the target image to be corrected (S1) and detects the position shift amounts between the partial images 61 (S3). And then, the CPU 41 acquires the assumed result of the motion component caused by the movement of the tissue 50, from the position shift amount detected in S3 (S14). Specifically, the CPU 41 acquires the function (for example, see FIG. 8) approximated to the transition of the position shift amounts detected in S3. The CPU 41 acquires a difference of the position shift amount from the value in the acquired function, as the assumed result of the motion component in the position shift amount. As a result, the motion component in the position shift amount is appropriately acquired using the function. The motion component acquired in S14 is the position shift amount, which is caused by the movement of the tissue 50, of each of the partial images 61 against the target image compared thereto.

Here, a method for acquiring the assumed result of the motion component in S14 may be modified. For example, the CPU 41 may acquire the shape component using various methods (for example, a method using a threshold described below, a method using a median filter, and the like) and then acquire a difference of the position shift amount against the acquired shape component, as the motion component in the position shift amount.

And then, the CPU 41 accumulates the motion components acquired in S14 to acquire an accumulated motion component (S15). The accumulated motion component indicates the position shift amount of each of the partial images 61 from the origin instead of the image compared thereto.

And then, the CPU 41 corrects the position of each of the partial images 61 into a position where the motion component detected in S14 is cancelled (S16). Specifically, the CPU 41 corrects the position of each of the partial images 61 forming the target image to be corrected (original image for which an alignment process or the like is not performed), into the position shifted from the image compared thereto by a distance corresponding to a value of the motion component for which its positive or negative is reversed. As a result, the assumed motion component is cancelled, so that the distortion of the target image to be corrected is appropriately corrected.

In S16, the position of each of the partial images 61 may be corrected using the accumulated motion component instead of the motion component. In this case, the CPU 41 corrects the position of each of the partial images 16 forming the target image to be corrected into a position shifted by a distance corresponding to a value of the accumulated motion component for which its positive or negative is reversed. As a result, the assumed motion component is cancelled. In a case in which the position of each of the partial images 61 is corrected using the motion component, the process of S15 may be omitted.

Another modification may be applied to the embodiment described above. For example, in S4 of the embodiment described above (see FIG. 5), the CPU 41 acquires the function f(y) approximated to the transition of the position shift amounts between the partial images 61 to acquire the assume result of the shape component in the position shift amount. However, the method for acquiring the assumed result of the shape component in the position shift amount may be modified. For example, the CPU 41 may delete, from the position shift amounts between the partial images 61, the position shift amount of which the difference from another position shift amount is equal to or larger than a threshold to acquire the assumed result of the shape component.

In this case, a relationship between a position shift amount to be determined whether it is deleted and the position shift amount compared thereto may be selected as needed. For example, the position shift amount compared thereto may be defined by the position shift amount adjacent to the position shift amount to be determined, in a direction in which the partial images 61 are arranged (Y direction in the embodiment described above). Further, the position shift amount compared thereto may be defined by the position shift amounts around the position shift amount to be determined.

Further, in a case in which the difference of the position shift amount is compared to the threshold and then the position shift amount of which the difference is equal to or larger than the threshold is deleted so as to acquire the shape component, the CPU 41 may perform an interpolation process that interpolates the deleted position shift amount, to the acquired shape component. In this case, the target image to be corrected is corrected based on the shape component without a blank (null), and thereby the accuracy of the correction is improved.

Further, the CPU 41 may perform a process that excludes an outlier from the position shift amounts detected in S3 to acquire the assumed result of the shape component in the position shift amount. In this case, the process that excludes the outlier may use, for example, the median filter or the like.

Further, in the embodiment described above, the derivative f(y), which is a curved line, is acquired from the position shift amount of the two-dimensional partial images 61, as the shape component, and the primitive function F(y), which is a curved line, is acquired from the acquired derivative f(y), as the accumulated shape component. However, the information of the accumulated shape component used as a reference for correcting the partial images 61 may indicate a curved surface instead of a curved line. For example, in a case that corrects the distortion of the three-dimensional target image to be corrected, the accumulated shape component that indicates a curved surface may be acquired based on the position shift amount of one-dimensional partial images (for example, one-dimensional partial image extending in the Z direction along the optical axis of the light).

Figure 12:
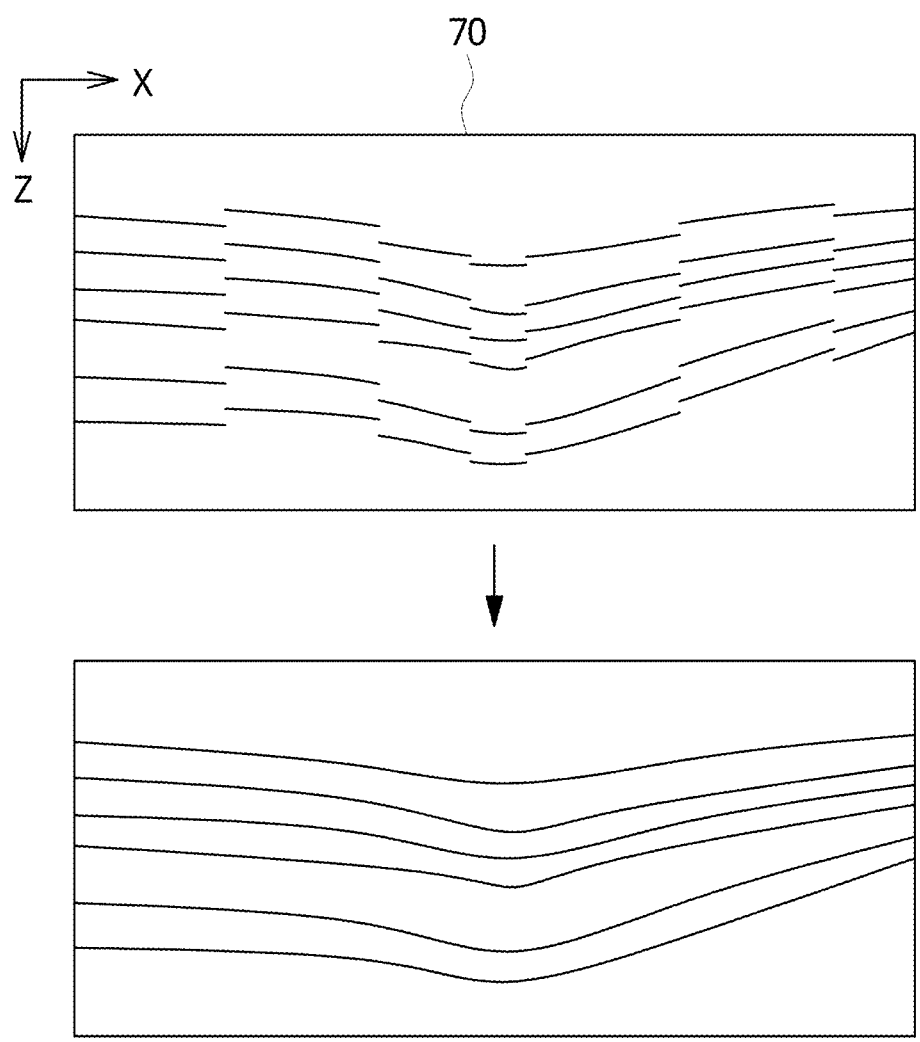
FIG. 12 is a view illustrating one example of a method for correcting the distortion of a two-dimensional target image 70 to be corrected.

Further, in the embodiment described above, the target image to be corrected is a three-dimensional image. However, the target image to be corrected may be a two-dimensional image. FIG. 12 is a view illustrating one example of a method for correcting the distortion of a two-dimensional target image 70 to be corrected. In the example shown in FIG. 12, the target image 70 to be corrected is a two-dimensional X-Z tomographic image photographed by scanning a subject with light in the X direction. When a tissue is moved during the scanning, as shown in FIG. 12, the two-dimensional target image 70 to be corrected might be distorted. The target image 70 to be corrected shown in FIG. 12 is generated by arranging the partial images in the X direction. The partial image may be a one-dimensional image extending in the Z direction (for example, one-dimensional image extending in the optical axis of the OCT measurement light (so-called A-scanning image)), or a two-dimensional image. The CPU 41 detects the position shift amounts between the partial images arranged in the X direction (S3) and acquires at least one of the shape component and the motion component (S4, S14). Thereafter, the CPU 41 corrects the position of each of the partial images based on the acquired component (S7, S16). As a result, the distortion of the two-dimensional image caused by the movement of the tissue is appropriately corrected. The two-dimensional target image to be corrected may be a two-dimensional front image that expands in a direction crossing the optical axis of the light, instead of a tomographic image.

The process that detects the position shift amount in S3 shown in FIG. 5 and FIG. 11 is one example of a process of "detecting position shift amounts". The process that acquires the assumed result of at least one of the shape component and the motion component in S4 shown in FIG. 5 and S14 shown in FIG. 11 is one example of a process of "acquiring a component". The process that corrects the position of each of the partial images 61 in S7 shown in FIG. 5 and S16 shown in FIG. 11 is one example of a process of "correcting". The process that acquires the accumulated shape component in S5 shown in FIG. 5 is one example of a process of "acquiring an accumulated shape component". The process that causes the storage device to store at least one of the shape component and the accumulated shape component in S8 shown in FIG. 5 is one example of a process of "storing a component". The process that corrects the position of each of the partial images in S2: YES, and S7 shown in FIG. 5 is one example of a process of "correcting afterward".

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

What is claimed is:

1. A medical image processing device that processes data of an image of a tissue of a living body, wherein the image is a two-dimensional image or a three-dimensional image generated by arranging data of partial images acquired by scanning the tissue of the living body with light and temporally continuously receiving the light from the tissue, the medical image processing device comprising a processor configured to:
  detect a position shift amount between the partial images forming the image;
  acquire a component that is an assumed result of at least one of a motion component, which is one component in the position shift amount caused by movement of the tissue during the scanning, and a shape component, which is another component in the position shift amount caused by a shape of the tissue, from the detected position shift amount; and
  correct a position of each of the partial images based on the acquired component in the position shift amount, wherein:
  the processor is configured to, in the process of acquire a component, acquire the assumed result of the shape component in the position shift amount; and
  the processor is configured to, in the process of correct a position, correct the position of each of the partial images for forming an aligned image for which the partial images are aligned, based on the shape component.

2. The medical image processing device according to claim 1, wherein the processor is configured to, in the process of detect a position shift amount, detect the position shift amount between the partial images based on a movement amount of each of the partial images when the each of the partial images is aligned.

3. The medical image processing device according to claim 2, wherein the processor is configured to, in the process of detect a position shift amount, detect the position shift amount between the partial images based on the movement amount of the each of the partial images when the each of the partial images is aligned into a position where similarity thereof to another partial image is equal to or larger than a threshold.

4. The medical image processing device according to claim 2, wherein the processor is configured to, in the process of detect a position shift amount, detect the position shift amount between the partial images based on the movement amount of the each of the partial images when the partial images are aligned such that positions of a specific tissue in the partial images among tissues photographed in the image are close to each other.

5. The medical image processing device according to claim 1, wherein the processor is configured to, in the process of acquire a component, acquire a function approximated to a transition of the position shift amount between the partial images, as the assumed result of the shape component in the position shift amount.

6. The medical image processing device according to claim 1, wherein the processor is configured to, in the process of acquire a component, acquire the assumed result of the shape component in the position shift amount by deleting, from the position shift amount between the partial images, a first position shift amount of which a difference from another position shift amount is equal to or larger than a threshold.

7. The medical image processing device according to claim 6, wherein the processor is configured to, in the process of acquire a component, perform an interpolation process that interpolates the deleted position shift amount, to the shape component acquired by deleting the position shift amount of which the difference is equal to or larger than the threshold.

8. The medical image processing device according to claim 1, wherein the processor is configured to, in the process of acquire a component, acquire a function approximated to a transition of the position shift amount between the partial images, and acquire a difference of the position shift amount from a value in the acquired function, as the assumed result of the motion component in the position shift amount.

9. The medical image processing device according to claim 1, wherein the processor is configured to acquire an accumulated shape component indicating an assumed shape of a tissue by accumulating the shape components acquired in the process of acquire a component.

10. The medical image processing device according to claim 1, wherein the processor is configured to:
  store a component by a storage device that is at least one of the shape component acquired in the process of acquiring a component and an accumulated shape component accumulating the shape components; and
  correct the position of each of the partial images based on a component relating to an image of which a subject to be photographed is the same as that of the image to be corrected, among the components stored in the storage device.

11. The medical image processing device according to claim 1, wherein the image is a three-dimensional image generated by arranging two-dimensional partial images expanding in a Z direction along an optical axis of the light and an X direction orthogonal to the Z direction, in a Y direction crossing the Z direction and the X direction.

12. A non-transitory computer-readable storage medium storing computer-readable instructions that, when executed by a processor of a medical image processing device that processes data of an image of a tissue of a living body, wherein the image is a two-dimensional image or a three-dimensional image generated by arranging data of partial images acquired by scanning the tissue of the living body with light and temporally continuously receiving the light from the tissue, causes the medical image processing device to perform processes comprising:
  detecting position shift amounts between the partial images forming the image;
  acquiring a component that acquires an assumed result of at least one of a motion component, which is one component in the position shift amount caused by movement of the tissue during the scanning, and a shape component, which is another component in the position shift amount caused by a shape of the tissue, from the detected position shift amount; and
  correcting a position of each of the partial images based on the acquired component in the position shift amount, wherein
  the processor is configured to, in the process of acquiring a component, acquire the assumed result of the shape component in the position shift amount; and
  the processor is configured to, in the process of correcting a position, correct the position of each of the partial images for forming an aligned image for which the partial images are aligned, based on the shape component.

13. A medical image processing device that processes data of an image of a tissue of a living body, wherein the image is a two-dimensional image or a three-dimensional image generated by arranging data of partial images acquired by scanning the tissue of the living body with light and temporally continuously receiving the light from the tissue, the medical image processing device comprising a processor configured to:
  detect a position shift amount between the partial images forming the image;
  acquire a component that is an assumed result of at least one of a motion component, which is one component in the position shift amount caused by movement of the tissue during the scanning, and a shape component, which is another component in the position shift amount caused by a shape of the tissue, from the detected position shift amount; and
  correct a position of each of the partial images based on the acquired component in the position shift amount,
  wherein the processor is configured to, in the process of acquire a component, acquire a function approximated to a transition of the position shift amount between the partial images, as the assumed result of the shape component in the position shift amount.

* * * * *

UNITED STATES PATENT AND TRADEMARK OFFICE
CERTIFICATE OF CORRECTION

| | | |
|---|---|---|
| PATENT NO. | : 11,602,276 B2 | Page 1 of 1 |
| APPLICATION NO. | : 16/833723 | |
| DATED | : March 14, 2023 | |
| INVENTOR(S) | : Kumagai et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 357 days.

Signed and Sealed this
Thirty-first Day of December, 2024

Derrick Brent
*Acting Director of the United States Patent and Trademark Office*